United States Patent
Barberio

(10) Patent No.: US 9,554,944 B2
(45) Date of Patent: Jan. 31, 2017

(54) MEDICAL PROTRUDED PADS OR DRESSINGS FOR WOUND CARE INCLUDING USE WITH ORTHOPEDIC AND PROSTHETIC DEVICES

(71) Applicant: Alessandro Barberio, Aurora (CA)

(72) Inventor: Alessandro Barberio, Aurora (CA)

(73) Assignee: Alessandro Barberio, Ontario (CA)

( * ) Notice: Subject to any disclaimer, the term of this patent is extended or adjusted under 35 U.S.C. 154(b) by 288 days.

(21) Appl. No.: 13/970,940

(22) Filed: Aug. 20, 2013

(65) Prior Publication Data

US 2014/0052041 A1 Feb. 20, 2014

Related U.S. Application Data

(60) Provisional application No. 61/742,742, filed on Aug. 20, 2012, provisional application No. 61/956,970, filed on Jun. 21, 2013, provisional application No. 61/958,758, filed on Aug. 6, 2013.

(51) Int. Cl.
  *A61F 13/00* (2006.01)
  *A61F 13/02* (2006.01)

(52) U.S. Cl.
  CPC ... *A61F 13/00042* (2013.01); *A61F 13/00017* (2013.01); *A61F 13/00021* (2013.01); *A61F 13/0209* (2013.01)

(58) Field of Classification Search
  CPC .............. A61F 13/00042; A61F 13/00021; A61F 13/00025; A61F 13/00029; A61F 13/0216; A61F 13/022; A61F 13/0223
  USPC ............................. 602/47, 58–59
  See application file for complete search history.

(56) References Cited

U.S. PATENT DOCUMENTS

| | | |
|---|---|---|
| 2,373,802 A | 4/1945 | Anderson |
| 3,850,167 A | 11/1974 | Seeley |
| 4,898,160 A | 2/1990 | Brownlee |
| 5,468,219 A | 11/1995 | Crippen |
| 5,507,792 A | 4/1996 | Mason et al. |
| 5,643,187 A * | 7/1997 | Naestoft ............ A61F 13/02 602/43 |
| 5,916,184 A | 6/1999 | McKeel |

(Continued)

FOREIGN PATENT DOCUMENTS

| | | |
|---|---|---|
| CA | 2 254 492 A1 | 5/2000 |
| CA | 2 355 041 A1 | 10/2002 |

(Continued)

OTHER PUBLICATIONS

Notification of Transmittal of the International Search Report and the Written Opinion of the International Searching Authority, or Declaration, dated Jul. 17, 2014.

*Primary Examiner* — Kari Petrik

(57) ABSTRACT

Methods and devices for dressing a wound are disclosed. One such dressing includes a layer of spaced protrusions, each protrusion shaped to receive medication for treating a wound and a plurality of holes defined in the layer, the holes configured to allow evaporation of exudate from the wound. Another such dressing includes multiple layers, each layer sandwiched over the next and including spaced protrusions, with alternate layers comprising absorptive materials. The alternate layers of absorptive materials can communicate via holes in the non-absorptive layers to allow exudate to travel from between the absorptive layers and away from the wound.

3 Claims, 14 Drawing Sheets

(56) References Cited

U.S. PATENT DOCUMENTS

| | | | |
|---|---|---|---|
| 6,482,491 | B1 | 11/2002 | Samuelsen et al. |
| 6,547,751 | B1 | 4/2003 | Barberio |
| 6,616,622 | B1 | 9/2003 | Barberio |
| 7,229,425 | B2 | 6/2007 | Dunagan |
| 7,250,034 | B2 | 7/2007 | Barberio |
| 8,012,112 | B2 | 9/2011 | Barberio |
| 2002/0115972 | A1* | 8/2002 | Dabi .................. A61F 13/0203 604/383 |
| 2004/0127838 | A1 | 7/2004 | Jeziak |
| 2004/0162511 | A1 | 8/2004 | Barberio |
| 2009/0018481 | A1 | 1/2009 | Bader |
| 2009/0093779 | A1 | 4/2009 | Riesinger |
| 2010/0268144 | A1 | 10/2010 | Lu et al. |
| 2011/0152735 | A1* | 6/2011 | Barberio ................ A61F 5/05 602/14 |
| 2011/0183109 | A1 | 7/2011 | Seyler et al. |
| 2011/0230848 | A1* | 9/2011 | Manwaring ......... A61M 1/0088 604/290 |
| 2013/0012897 | A1 | 1/2013 | Collyer |

FOREIGN PATENT DOCUMENTS

| | | |
|---|---|---|
| CA | 2 478 159 A1 | 2/2006 |
| CA | 2 478 162 A1 | 2/2006 |
| CN | 202844054 U | 4/2013 |
| CN | 202960940 U | 6/2013 |
| CN | 203122770 U | 8/2013 |
| DE | 101 28 230 A1 | 6/2002 |
| DE | 20 2010 012704 U1 | 12/2010 |
| EP | 1 496 826 A1 | 1/2005 |
| EP | 1 640 023 A1 | 3/2006 |
| EP | 2 253 294 A1 | 11/2010 |
| FR | 2583636 A1 | 12/1986 |
| JP | 2000-213656 A | 8/2000 |
| JP | 2004-208972 A | 7/2004 |
| JP | 2010-131163 A | 6/2010 |
| WO | 2006/136024 A1 | 12/2006 |
| WO | 2008083477 | 7/2008 |
| WO | 2009/047564 A2 | 4/2009 |

\* cited by examiner

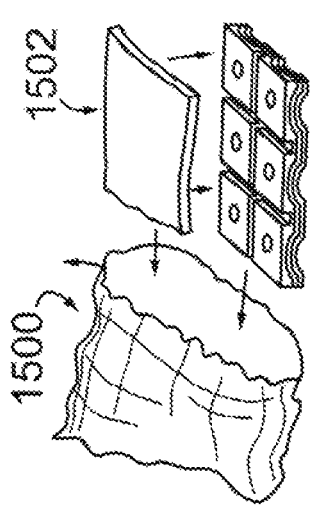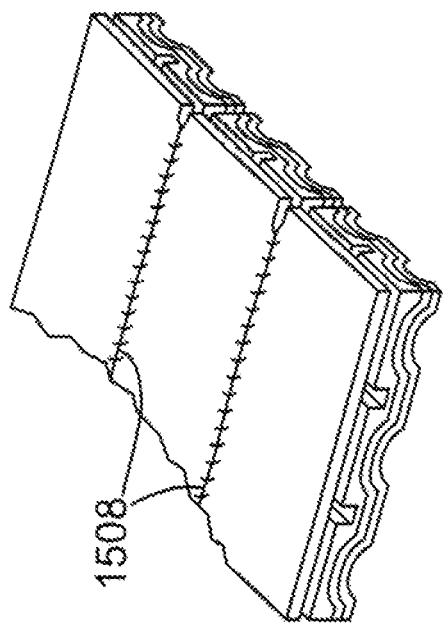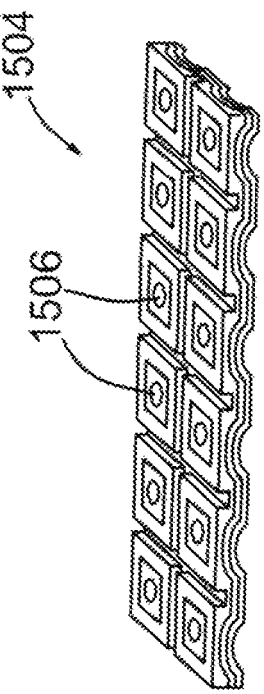

MEDICAL PROTRUDED PADS OR DRESSINGS FOR WOUND CARE INCLUDING USE WITH ORTHOPEDIC AND PROSTHETIC DEVICES

CROSS-REFERENCE TO RELATED APPLICATION

This application claims the benefit of U.S. Provisional Patent Application Ser. No. 61/742,742, filed Aug. 20, 2012. This application also claims the benefit of U.S. Provisional Patent Application Ser. No. 61/956,970, filed Jun. 21, 2013. This application also claims the benefit of U.S. Provisional Patent Application Ser. No. 61/958,758, filed Aug. 6, 2013. The contents of these applications are incorporated herein by reference.

FIELD OF THE INVENTION

The present invention relates generally to the field of wound treatment and medical uses of treatment devices for the same.

BACKGROUND OF THE INVENTION

Today, wounds are treated with great care, but dermatologists do not always agree on the procedures for wound treatment. Wounds need to breathe, having access to oxygen and a moist environment. But, with current procedures for wound treatment and existing wound care supplies, wounds do not receive enough oxygen or adequate moisture to heal. Frequent applications of new dressings and medication are needed and can be costly.

An example procedure from providing moisture to the wound is to cover the wound with a hydrogel pad. This pad is designed to keep the wound moist, but, because of its lack of absorption, a hydrogel pad may not be an appropriate choice for moderately weeping wounds as the hydrogel pad does not always provide sufficient moisture to heal open wounds.

The embodiments in this application improve and extend the second part of European Patent Application No. 08706194.1 describing a mini-perforated sheet made of the bumpy or protruded layer. The '194.1 application describes the layer as comprising ethylene-vinyl acetate (EVA) made from medical sterilized silicone in combination with different materials of different hardness.

SUMMARY OF THE INVENTION

One aspect of the disclosed embodiments is a wound dressing. The wound dressing includes a layer including spaced protrusions. Each protrusion is shaped to receive medication for treating a wound. The wound dressing also includes a plurality of holes defined in the layer. Each of the holes is configured to allow evaporation of exudate from the wound.

Another aspect of the disclosed embodiments is a multi-layered wound dressing. The multi-layered wound dressing includes a first layer comprising absorptive material for application proximate to a wound and a second layer comprising non-fluid permeable material disposed above the first layer. The multi-layered wound dressing also includes a third layer comprising absorptive material disposed above the second layer and a fourth layer comprising non-fluid permeable material disposed above the third layer. Each of the layers includes spaced protrusions. The multi-layered wound dressing also includes a plurality of spaced rings each extending from inner walls of the spaced protrusions of the second layer, the spaced rings configured to collect exudate. Additionally, the multi-layered wound dressing includes a plurality of holes defined in the spaced protrusions of the second layer, the holes configured to allow exudate to pass from the first layer to the third layer.

Other advantages, features and characteristics of the present invention, as well as methods of operation and functions of the related elements of the structure, and the combination of parts and economies of manufacture, will become more apparent upon consideration of the following detailed description and the appended claims with reference to the accompanying photographs, the latter being briefly described hereinafter.

BRIEF SUMMARY OF THE DRAWINGS

The description herein makes reference to the accompanying drawings wherein like reference numerals refer to like parts throughout the several views and wherein:

FIGS. 15A-E show a sequence representing the construction of a multi-layered dressing such as the multi-layered dressing shown in FIG. 12;

DETAILED DESCRIPTION OF THE ILLUSTRATIVE EMBODIMENT

Existing wound dressings and treatments that covers the foot or leg can become very hot and uncomfortable and can cause the patient to perspire unnecessarily. This disclosure describes various embodiments of an improved multi-perforated pad or dressing, for example, partially made of medical silicone. The pad or dressing is designed to allow air to pass through it and the reach the area of a wound. The pad or dressing is also designed to be flexible and capable of covering irregular shapes associated with the body of a human or animal.

The pads or dressings described in the below embodiments can deliver medication, provide ventilated support, and rapidly absorb and lock away exudate, all while keeping bacteria away from a wound and decreasing the risk of maceration of a patient's skin. Additionally, the improved pads and dressings have an overall lower cost based on the decreased number of dressing changes necessary to provide treatment to a patient's wound.

Figure 1:
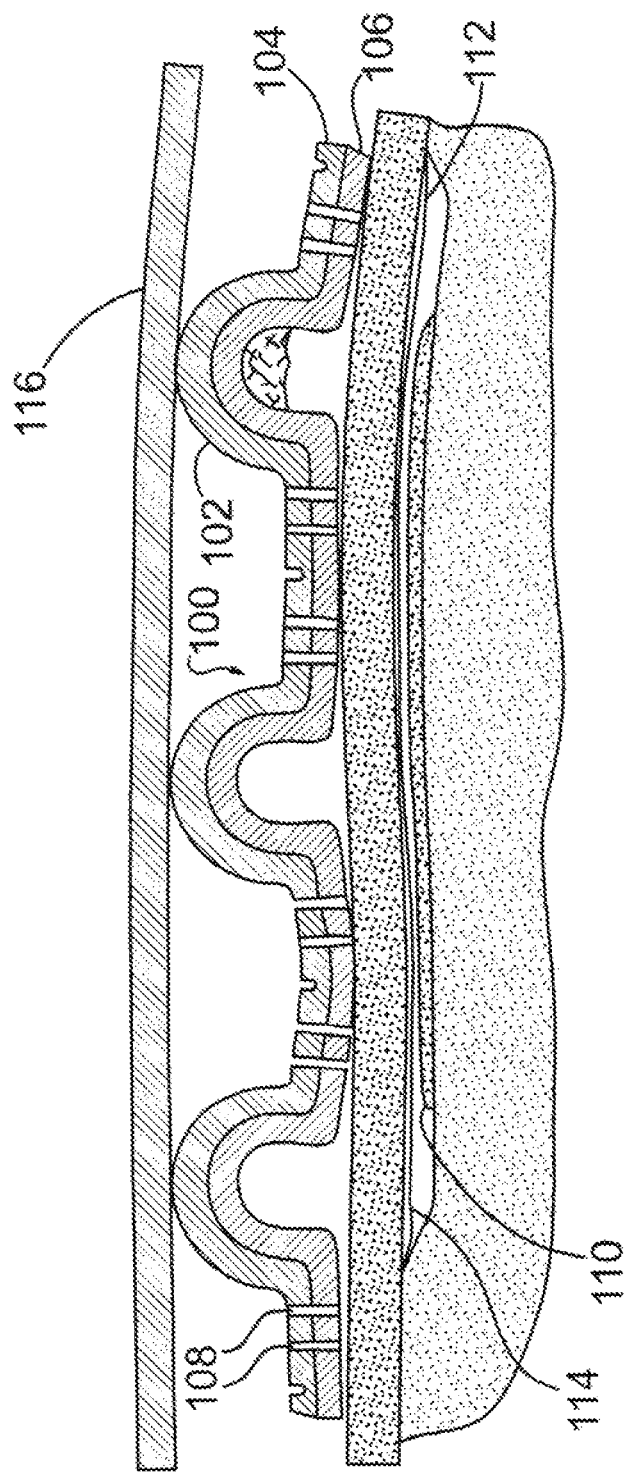
FIG. 1 is an example embodiment of a pad or dressing for treating and dressing wounds.

FIG. 1 is an example embodiment of a pad or dressing 100 for treating and dressing wounds. Many types of wounds can be treated with the pad or dressing 100 described both in this example and the pads or dressings described in the additional example embodiments below. For example, blisters, burns, lesions, bed sores, venous ulcers, arterial ulcers, post-operative wounds, edema inside casted limbs, and exuding wounds of superficial, deep, chronic, or acute nature can be treated. The pad or dressing 100 can be used for aeration and medication inside the walls of walking braces, to replace treatment foams, as part of a wrist brace, or as the internal wall of a prosthetic device.

The pad or dressing 100 can be designed with protrusions or bumps 102. The pad or dressing 100 can consist of a layer 104 made of EVA or medical silicone and a layer 106 made of medical sterilized silicone. The layers 104, 106 can alternatively be formed of one or more nanofibers, for example, polyvinylalcohol, chitosan, carboxymethylcellulose gelatin, collagen, hyaluronic acid, or polyurethane. The layers 104, 106 can be manufactured as a single piece, or separately, and are also known as backings for the pad or dressing 100. The protrusions or bumps 102 can be equally spaced by a distance of approximately one centimeter. A series of holes 108 are disposed proximate to the protrusions or bumps 102. The diameters of these holes 108 can, for example, range from 0.5 to 1 mm.

As shown in FIG. 1, a wound 110 can be covered by an antibiotic or equivalent sterilizer 112 such as Aquafor™. On top of the sterilizer 112, a hydrogel sheet 114 for assisting the maintenance of a moist environment can be applied. Hydrogel sheets 114 are cross-linked polymer gels. Some hydrogel sheets 114 are available with an adhesive border. In this instance, the hydrogel sheets 114 can be applied as narrow strips separated equidistantly by 1 cm. The use of narrow strips of hydrogel sheets 114 allows the section of the wound 110 that is not covered by the hydrogel sheet 114 to receive more oxygen penetration from the outside through the series of holes 108.

Because of the empty space beneath the protrusions or bumps 102, there remains room for oxygen and moisture. One of the many advantages of this embodiment is that the protrusions or bumps 102 and the holes 108 both contribute to the wound 110 having more moisture and more oxygen, allowing the pad or dressing 100 to fight anaerobic bacteria, including odorous bacteria. By the addition of oxygen to the wound via the series of holes 108, such wounds 110 as diabetic ulcers can avoid the disadvantageous application of hyperbaric oxygen therapy. The flow of air that travels through the series of holes 108 can be regulated by applying an external cover or sheet 116 of a hydrophobic nature. This sheet 116 can be made of medical foam or silicone.

The dimensions of pad or dressing 100 can be scaled depending on its use, for example, made larger or smaller overall. The pad or dressing 100 is suitable for use in dressing and treating wounds in both humans and animals. The pad or dressing 100 can also be used as an immobilizing cast for aerobic ventilation or for decompression of limbs to prevent edema. The pad or dressing 100 can also be used in many prosthetic devices or inside the walls of walking shoes. Most importantly, it will be used inside the walls of any walking brace, thus replacing the foam that surrounds the foot or leg of the patient. The pad or dressing 100 can also be washable.

Figure 2:
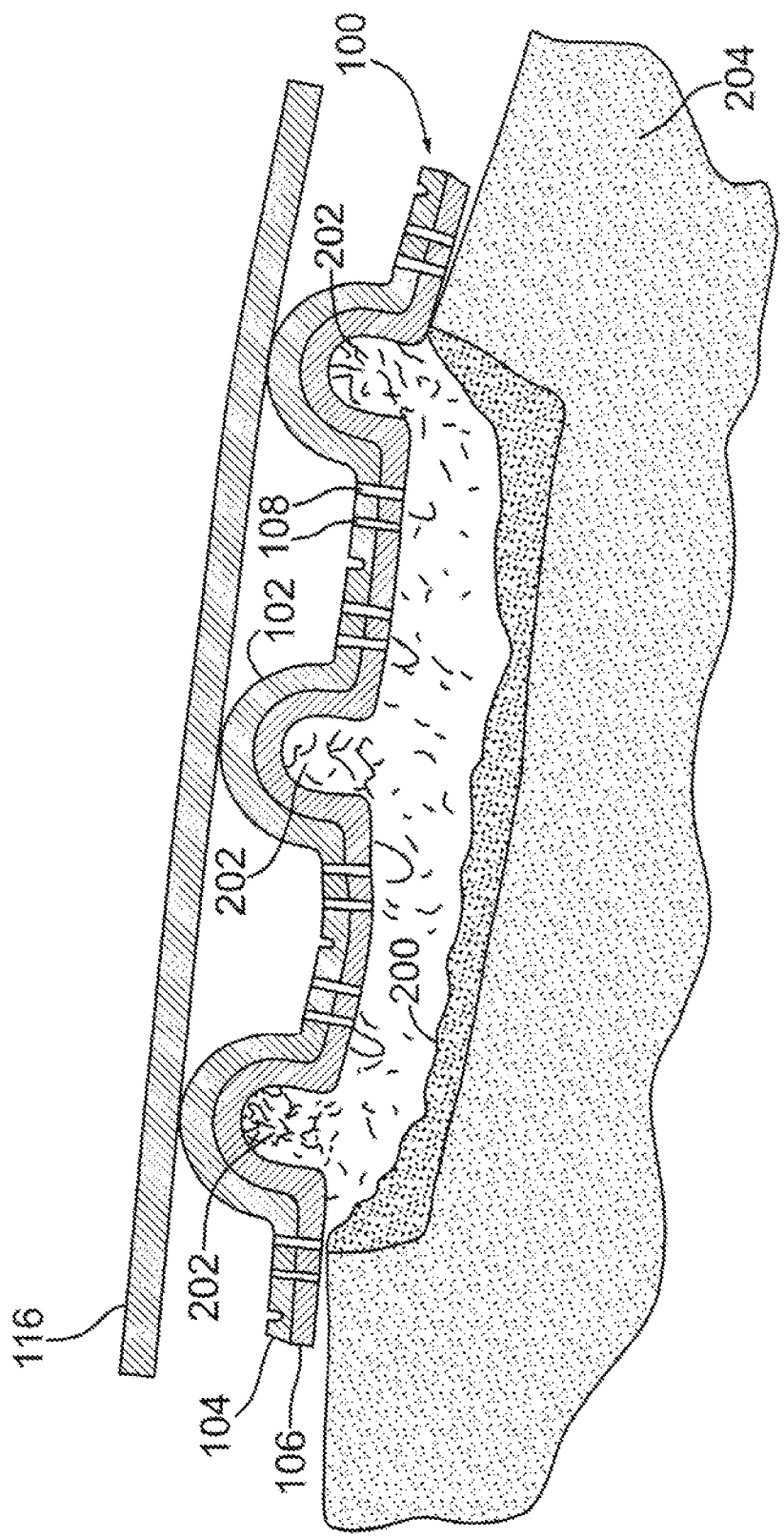
FIG. 2 is an alternative embodiment of the pad or dressing for treating and dressing wounds as described in FIG. 1.

FIG. 2 is an alternative embodiment of the pad or dressing 100 for treating and dressing wounds as described in FIG. 1. In this example, a deep wound 200 is shown. Given the depth of the wound 200, the holes 108 are not as important for wound breathing purposes. In fact, the pad or dressing 100 as shown in this embodiment can be used with or without holes 108. The protrusions or bumps 102 can be filled with a hydrogel paste 202, the hydrogel paste 202 providing moisture as needed due to the size of the wound. No hydrogel paste 202 is necessary in the regions between the protrusions or bumps 102. Avoiding application of the hydrogel paste 202 in the areas between the protrusions or bumps 102 ensures that the series of holes 108 will be free to allow air to enter the pad or dressing 100 and reach skin 204 or the wound 200. The pad or dressing 100 thus allows the wound 200 to receive the hydrogel paste 202 that is stored inside each protrusion or bump 102 to speed healing and allow for the pad or dressing 100 to be changed less often.

The pad or dressing 100 can be made of a medical sterilized silicone. The pad or dressing 100 can also be made of two layers of silicone, each of a different hardness. In some embodiments, the harder layer is toward the top. A second layer of an EVA material can also be added to the pad or dressing 100. The EVA material can help the pad or dressing 100 to withstand external pressure should the patient make contact with an external object. Additionally, adhered strips of cotton can be applied between the protrusions or bumps 102. The application of these cotton strips can allow medication to adhere more easily to the pad or dressing 100 while facilitating mess-free handling by medical professionals.

The medications used inside pad or dressing 100 can also vary. For example, a hydrocolloid paste can be used for shallow wounds or several layers of cotton can be used for deep wounds, such as wound 200. Different or additional dressings can be also be used in the protrusions or bumps 102, depending on the severity of the wound. The pads or dressings 100 can also be constructed such that differing medications are present in each of the protrusions or bumps 102, the medications being existing medications known to medical professionals and those yet to be developed.

The pad or dressing 100 shown in FIG. 2 also includes layers 104, 106 constructed of medical silicone and EVA, respectively. Alternatively layers 104, 106 can be constructed of a breathable TPU film. The TPU film can allow the wound 200 to receive air vapor and oxygen but will also protect the wound 200 from germs and bacteria. In this alternative construction, the holes 108 are important for transmission of air from outside of the pad or dressing 100. Other materials possible for construction of the backing layers 104, 106 include Pellethane™ or Saran™, for example, in use with small wounds. Additionally, the external cover or sheet 116 in this embodiment can be gauze, a tubular stokinette, or a tubular net such as Surgilast™. The cover or sheet 116 can be excluded when flat or small areas are being treated.

Figure 3:
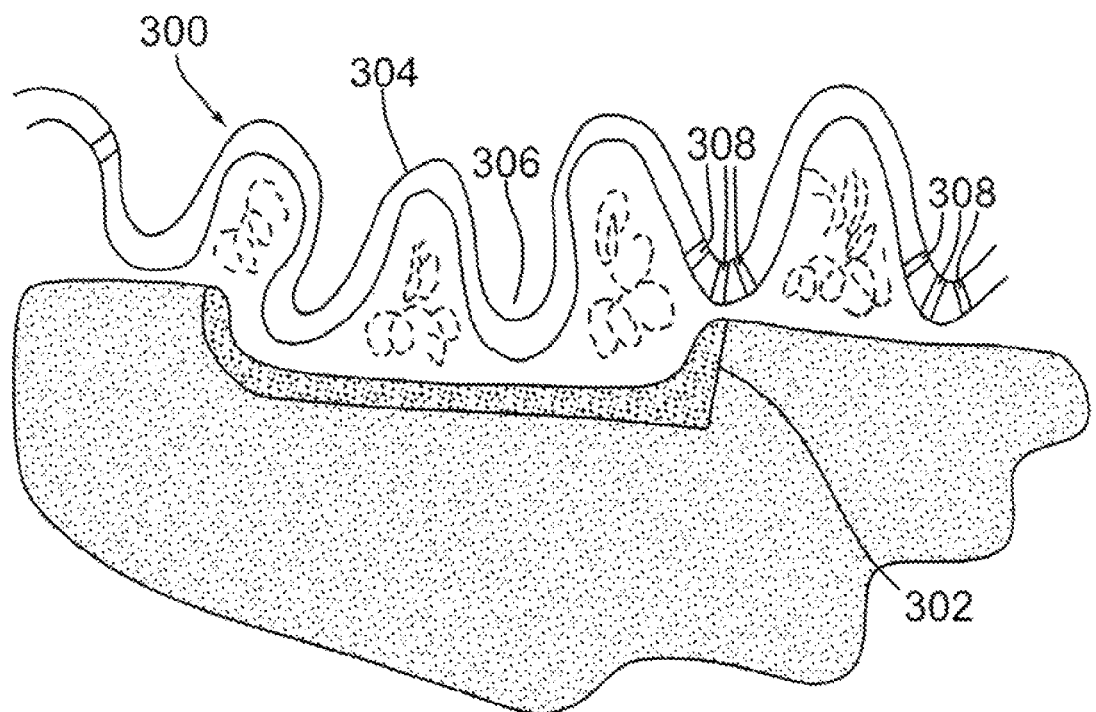
FIG. 3 is another example embodiment of a pad or dressing for treating and dressing wounds.

FIG. 3 is another example embodiment of a pad or dressing 300 for treating and dressing wounds 302. In this example embodiment, the pad or dressing 300 includes multiple, closely spaced protrusions 304, 306. The crest of protrusion 304, for example, is of equal size to the crest of protrusion 306 but is reversed in shape along the length of the pad or dressing 300, creating an alternating pattern of crests. This embodiment of the pad or dressing 300 is configured for dressing and treatment of deeper wounds, such as wound 302, and will adapt or sink more easily inside the cavity of the wound 302. In a similar manner as the pad or dressing 100 described in FIG. 1, this pad or dressing 300 can also be made of more than one layer and medications can be pre-packed within the protrusions 304, 306. The medications can be in the form of pastes, dressings, or meshes. The pad or dressing 300 can also include holes 308 at positions at the crest or around the protrusions 304, 306 if there is no medication inside the protrusions 304, 306.

Figure 4:
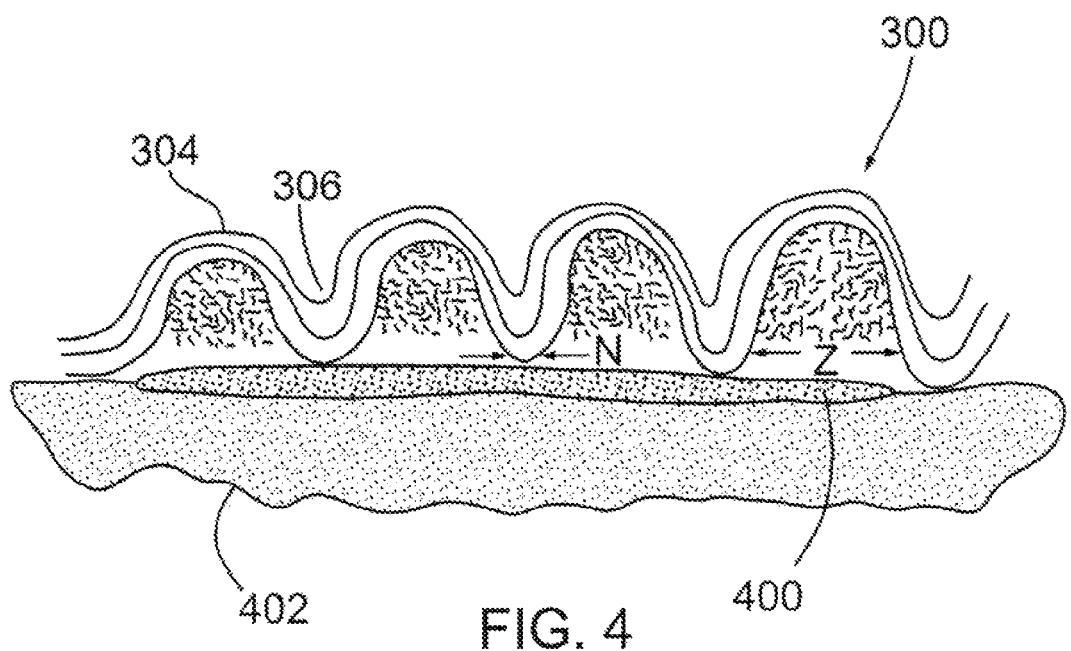
FIG. 4 is an alternative embodiment of the pad or dressing for treating and dressing wounds as described in FIG. 3.

FIG. 4 is an alternative embodiment of the pad or dressing 300 for treating and dressing wounds as described in FIG. 3. In this alternative embodiment, the pad or dressing 300 is covering a shallow, flat wound 400. A shallow, flat wound 400 requires a lot of medication; therefore, each protrusion 304, 306 can be filled with the appropriate kind of medication. The height of the protrusions 304, 306 can vary, and more medicated paste is need in the larger, taller protrusions. Larger protrusions can allow the patient's skin 402 to receive a higher concentration of medication. Using pads or dressings 300 with this design can save money because the pads or dressings 300 will need to be changed less frequently. This design also has the advantage of covering a large wound area with medication because distance Z along the internal cavity of a protrusion is much larger than the distance W where no medication is present.

Figure 5:
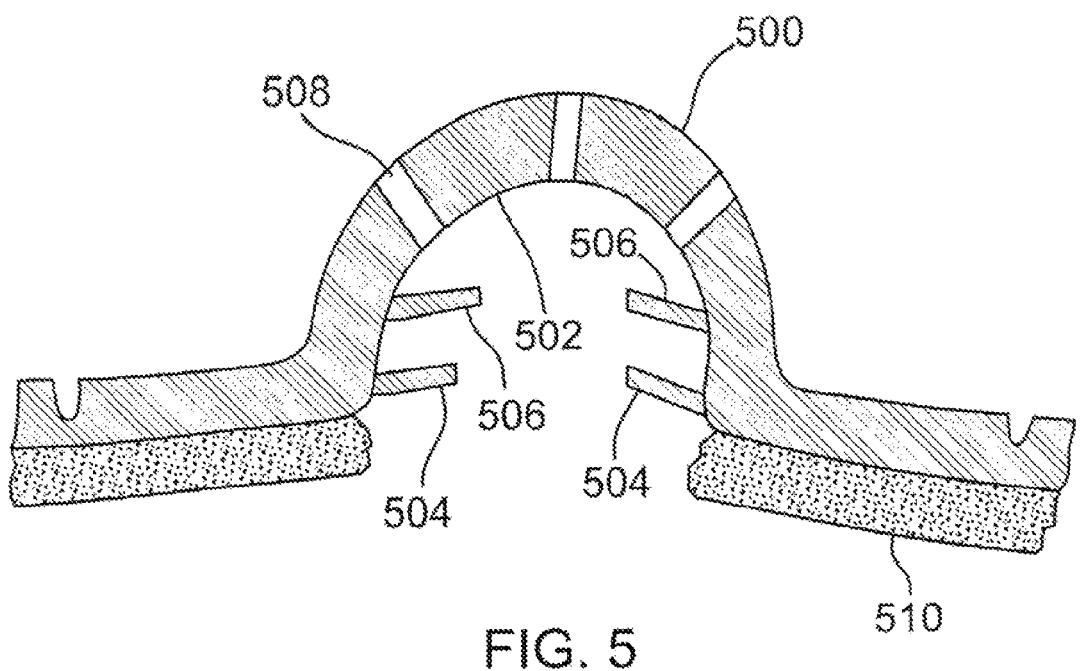
FIG. 5 is an example embodiment of a protrusion configured for use with any of the pads or dressings of FIGS. 1-4.

FIG. 5 is an example embodiment of a protrusion 500 configured for use with any of the pads or dressings of FIGS. 1-4. The protrusion 500 is shown in cross-section. In this example, the protrusion includes an internal cavity 502 and a pair of spaced rings 504, 506 circling the walls of the internal cavity 502. Each of the spaced rings 504, 506 are angled, for example, at 30 degrees to the walls of the internal cavity 502, stretching toward the crest of the protrusion 500. The function of the spaced rings 504, 506 is further described below. The protrusion 500 may also include a series of holes 508, though the holes 508 are not required. The lower layer 510 that forms part of the pad or dressing can be an absorptive material.

Figure 6:
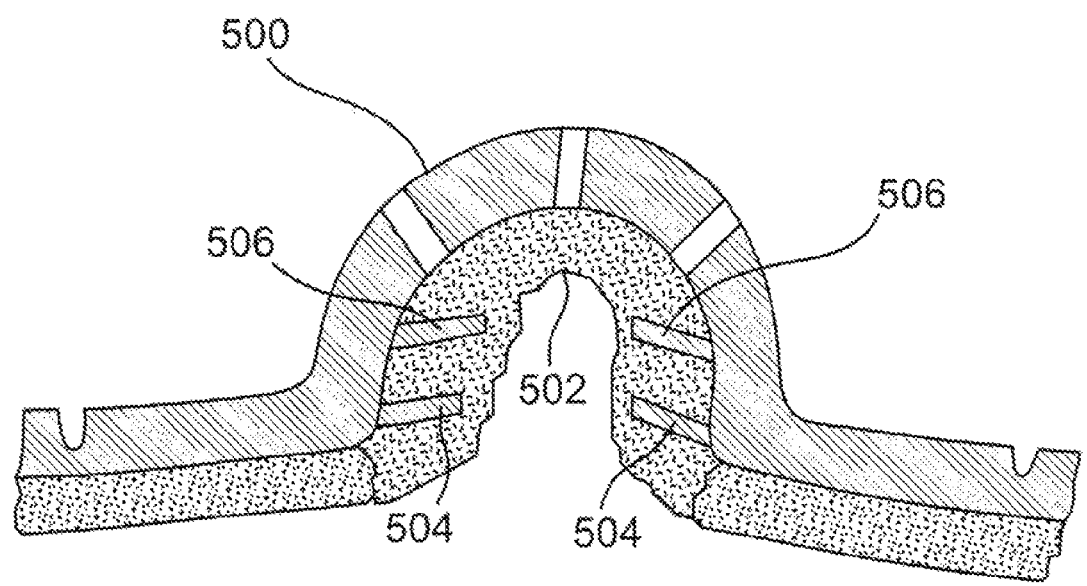
FIG. 6 is an alternative embodiment of the protrusion of FIG. 5.

FIG. 6 is an alternative embodiment of the protrusion 500 of FIG. 5. In this example, the lower layer 510 that forms part of the pad or dressing extends along the walls of the internal cavity 502 of the protrusion 500, covering the spaced rings 504, 506. Again, the lower layer 510 can be formed of absorptive material.

Figure 7:
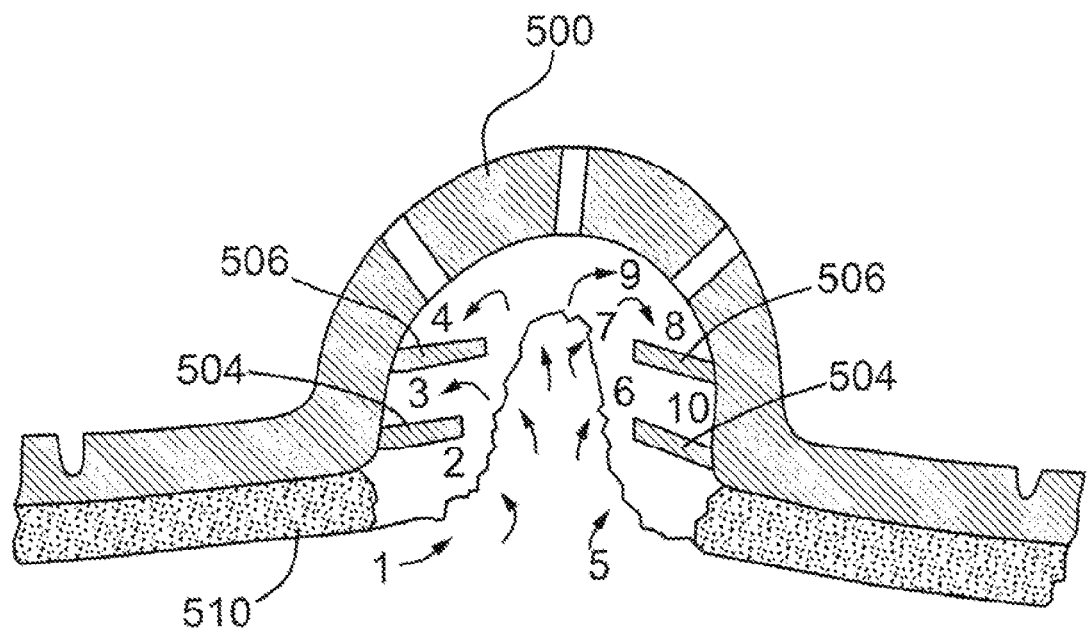
FIG. 7 shows the trajectory of vapors and liquids traveling within the protrusion of FIG. 5.

FIG. 7 shows the trajectory of vapors and liquids traveling within the protrusion 500 of FIG. 5. Vapors produced while a wound heals can include evaporated exudate and the liquids produced can include molecules of liquid coming from the wound that can saturate the absorptive material of the lower layer 510. If the exudate or liquid molecules from the wound excessively accumulate on the lower layer 510 of the pad or dressing, the lower layer 510 can become saturated with unwanted organisms and liquid or vapor can wick around the edges of the pad or dressing, leading to unwanted odors and maceration of a patient's skin. In addition, once too much liquid accumulates on the lower layer 510, it can seep back toward the wound. The protrusion 500 shown in this example is designed to avoid excess exudate returning to the wound.

The spaced rings 504, 506 of the protrusion 500 can capture exudate and liquid from the cavity or surface of the wound. The trajectory of the exudate and liquid from the wound to the spaced rings 504, 506 is represented with arrows numbered one through ten. The path starts at arrow one and continues through arrow ten, depositing excess materials within the spaced rings 504, 506 based on the upward facing direction of the spaced rings 504, 506, in this example, at an angle of approximately 30 degrees in respect to the wall of the protrusion 500. Once the excess material is stored within the spaced rings 504, 506, it is not returned to the wound. The protrusion 500 and spaced rings 504, 506 can be of singular construction of silicone, polyurethane, polyamide, polyester, EVA, gel, plastazote, plastic, cork, foam, or any other hypoallergenic material. Alternatively, the protrusion 500 and spaced rings 504, 506 can be separate layers of different materials.

The use of protrusions 500 of the style shown in FIG. 7 are beneficial in pads, dressings, or coverings for wounds where external pressure is expected to be applied, as the protrusions 500 shield the wound. The protrusions 500 can have a hard exterior and soft exterior, keeping them from compressing during external pressure, acting, as such, as a bumper when a patient faces a situation where pressure is applied to the protrusion 500. Further, the use of protrusions 500 with pads, dressings, or coverings for wounds can capture more exudate or liquid than would a flat-surface style dressing, as there is more surface area on the curved surfaced of the protrusions 500. Given the additional exudate or liquid captured, fewer pads or dressings will be needed, saving money for the patient or caregiver.

Figure 8:
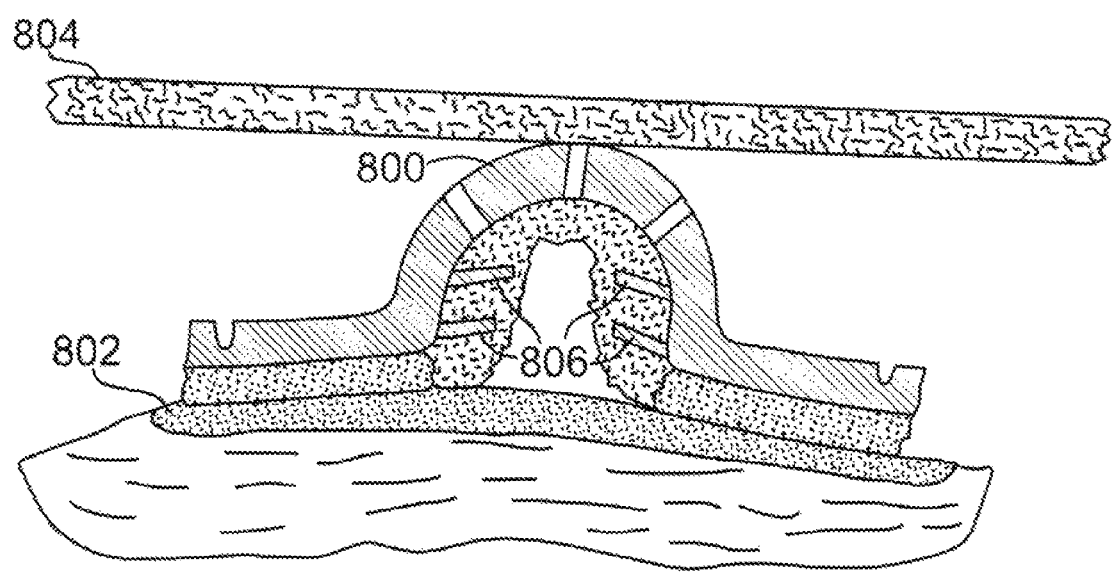
FIG. 8 is an example embodiment of a dressing for use in compressive therapy integrating a protrusion similar to the protrusion of FIG. 5.

FIG. 8 is an example embodiment of a dressing for use in compressive therapy integrating a protrusion 800 similar to the protrusion 500 of FIG. 5. Compressive therapy is used to apply uniform pressure to dressings, for example, to control leg ulcers or apply pressure to the bottom of a patient's foot. Prior art dressings used in compressive wound therapy allow exudate to wick across the dressing, affecting healthy tissue outside of the wound and causing maceration and unwanted odors. The dressing of FIG. 8 can be used to apply pressure to a wound 802, such as an ulcer, by means of an elastic strap 804.

The protrusion 800 in FIG. 8 is similar to the protrusion 500 of FIGS. 5-7 in that it includes spaced rings 806 that collect exudate and keep the exudate from flowing back into the wound 802. In this example, the spaced rings 806 extend at an angle of 15 degrees from the wall of the protrusion 800. The protrusion 800 and spaced rings 806 are designed not to collapse under the influence of external pressure and provide a larger layer of absorptive material that would be possible with a flat dressing. The shape of multiple protrusions 800 along a compressive dressing will act as a bumper, protecting the wound 802 from compression.

Figure 9:
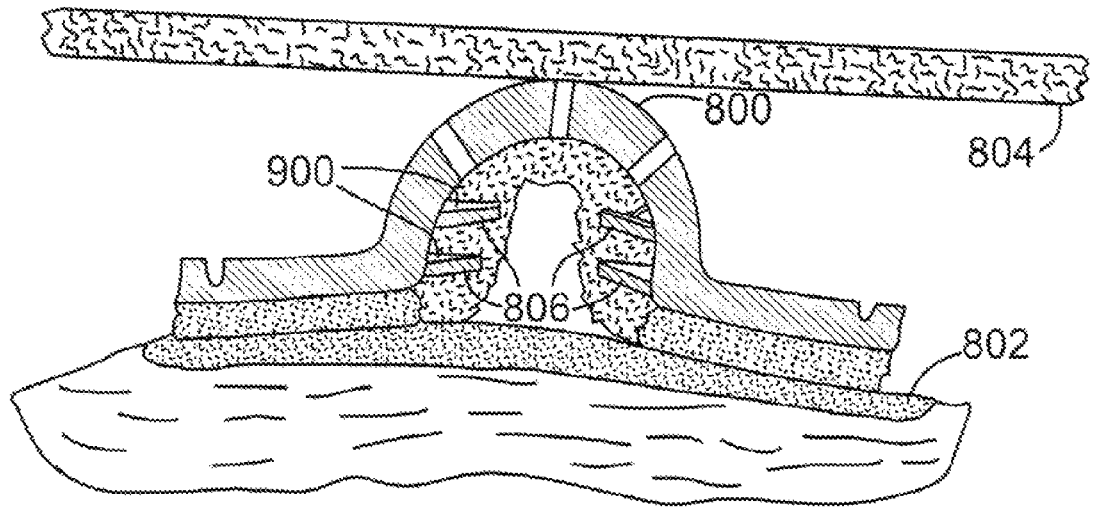
FIG. 9 shows the collection of exudate along the spaced rings of a protrusion of the dressing of FIG. 8.

FIG. 9 shows the collection of exudate 900 along the spaced rings 806 of a protrusion 800 of the dressing of FIG. 8. The exudate 900 can accumulate at different rates, the rate depending on the nature of the components of the exudate 900, the health of the patient using the dressing, the mechanism of exchanged gases passing through the dressing, etc. The inclusion of the spaced rings 806 allows collection of larger amounts of exudate 900 that would be possible with other dressings, minimizing the risk of leaks. In addition, exudate 900 from the wound 802 will force the absorptive layer to swell, which could cause the dressing to be a carrier of unwanted bacteria and odor, but, because the backing of the dressing is porous, it is antibacterial in nature and permeable to moisture and air, allowing the exudate 900 from the wound 802 to evaporate, once collected.

The dressings described in FIGS. 8 and 9 can be used with or without medications, and the medications can have a continuous or non-continuous spread along the dressing on the side proximate the patient's wound. The material of at least some of the layers of the dressing can be Coban,™ supporting flexibility of the dressing while at the same time keeping the dressing pressed to the patient's skin. The shape of the dressings can be tubular to allow coverage of limbs having mostly uniform diameter, or rectangular, square, oval, circular, concave, or any other shape configured to conform to the given wound. The dressings can also be framed with a backing carrying an adhesive allowing a medical professional to adhere the dressing to a wound. The adhesive can extend along all or most of the perimeter of the backing, with the exception of two small tab-style areas. The non-adhesive tab-style areas can be used to remove the dressing without damaging the skin, for example, as could occur caused by a medical provider's nails when the medical provider attempts to dig under a corner of the dressing for removal.

Figure 10:
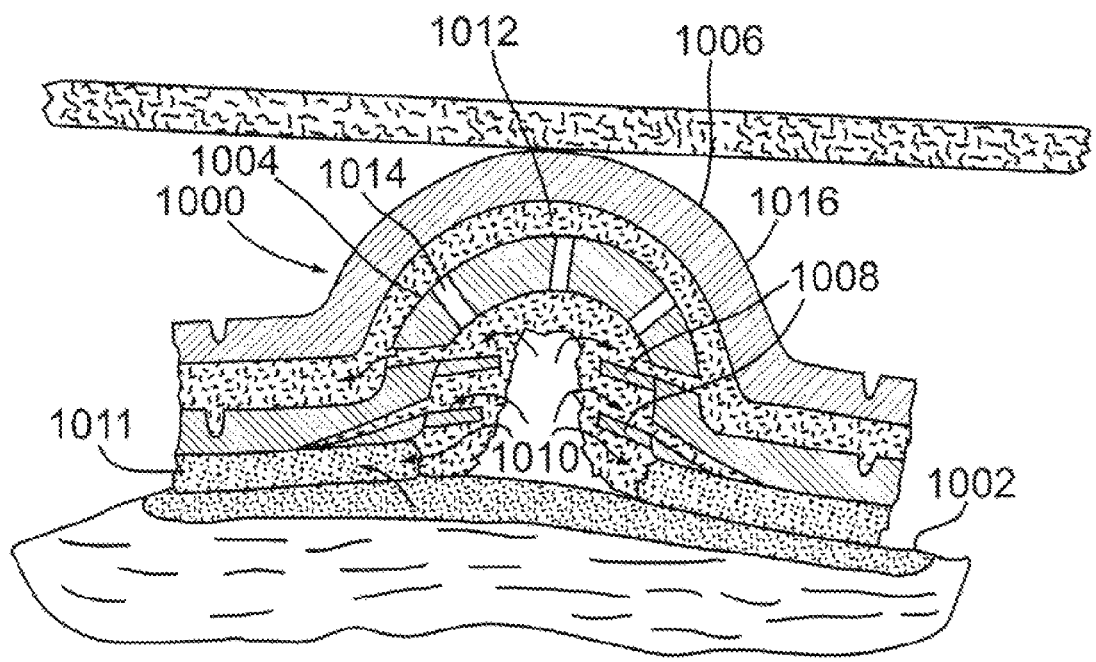
FIG. 10 is an example embodiment of a protrusion configured for use with a multi-layered pad or dressing.

FIG. 10 is an example embodiment of a protrusion 1000 configured for use with a multi-layered pad or dressing. The protrusion 1000 is designed to handle high levels of exudate seeping from the wound 1002. The pad or dressing including protrusion 1000 can include both a first outer layer 1004 and a second outer layer 1006, where exudate can be collected both below the first outer layer 1004 and between the first outer layer 1004 and the second outer layer 1006. The first outer layer 1004 and second outer layer 1006 are made of materials that are generally not permeable to exudate. The protrusion 1000 includes spaced rings 1008 extending at an angle to the inside wall of the protrusion 1000 in a similar manner to the protrusions described in previous embodiments. However, at the junction of the wall formed by the first outer layer 1004, openings are present, allowing exudate to flow both between the first outer layer 1004 and the second outer layer 1006 as well as into a recess within the first outer layer 1004.

The exudate is first absorbed directly from the wound 1002 on absorptive layer 1011 beneath the first outer layer 1004. The exudate drawn into protrusion 1000 is then further drawn into the storage space between the first outer layer 1004 and second outer layer 1006 as shown by absorption paths 1010. This exudate will not wick or leak back toward the wound 1002 based both on the non-compressibility of the protrusion 1000 and the presence of another absorptive layer 1012 between the first outer layer 1004 and second outer layer 1006. The direction of absorption of exudate thus starts at absorptive layer 1011, flows up into the protrusion 1000, along the edges of the spaced rings 1008, through the holes at the base of the spaced rings 1008, and onto the absorptive layer 1012. The protrusion 1000 includes holes 1014 and the second outer layer 1006 also includes holes 1016, allowing exudate collected in the protrusion 1000 and the absorptive layer 1012 to evaporate.

Though prior art dressings or pads can also use more than one layer of absorptive material to collect exudate, the danger of wicking or leaking during compression is still present in these prior art dressings. The shape and non-compressible nature of the protrusion 1000 alleviates this issue, and the openings along the spaced rings 1008 provide an efficient collection means to move exudate onto the mid-level absorptive layer 1012 without allowing the exudate to return to the wound 1002 during compression of the pad or dressing.

Figure 11:
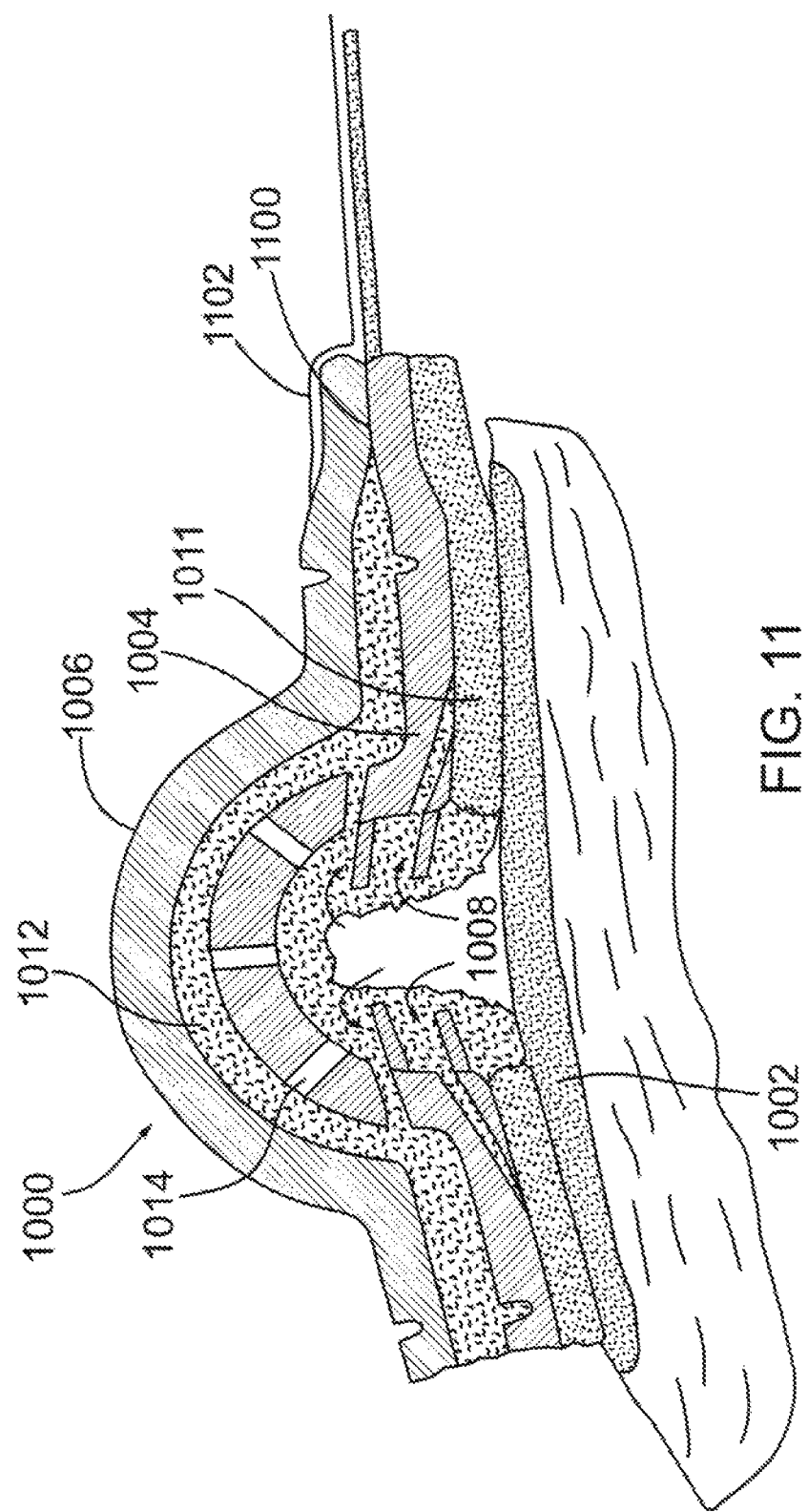
FIG. 11 is an example embodiment of a multi-layered dressing integrating the protrusion of FIG. 10.

FIG. 11 is an example embodiment of a multi-layered dressing integrating the protrusion 1000 of FIG. 10. The absorptive layer 1011, first outer layer 1004, spaced rings 1008, absorptive layer 1012, and second outer layer 1006 all function as described in FIG. 10. FIG. 11 is included to describe the assembly and application of the dressing. A weld 1100 or other attachment adheres the first outer layer 1004 to the second outer layer 1006, keeping exudate locked within the absorptive layer 1012. An adhesive layer 1102 is also attached to the second outer layer 1006 for adhering the dressing to a patient's skin. As was the case with previously described dressing embodiments, the size of the multi-layered dressing can be scaled to the size of the wound 1002, and the adhesive layer 1102 can be scaled to the size of the dressing.

Figure 12:
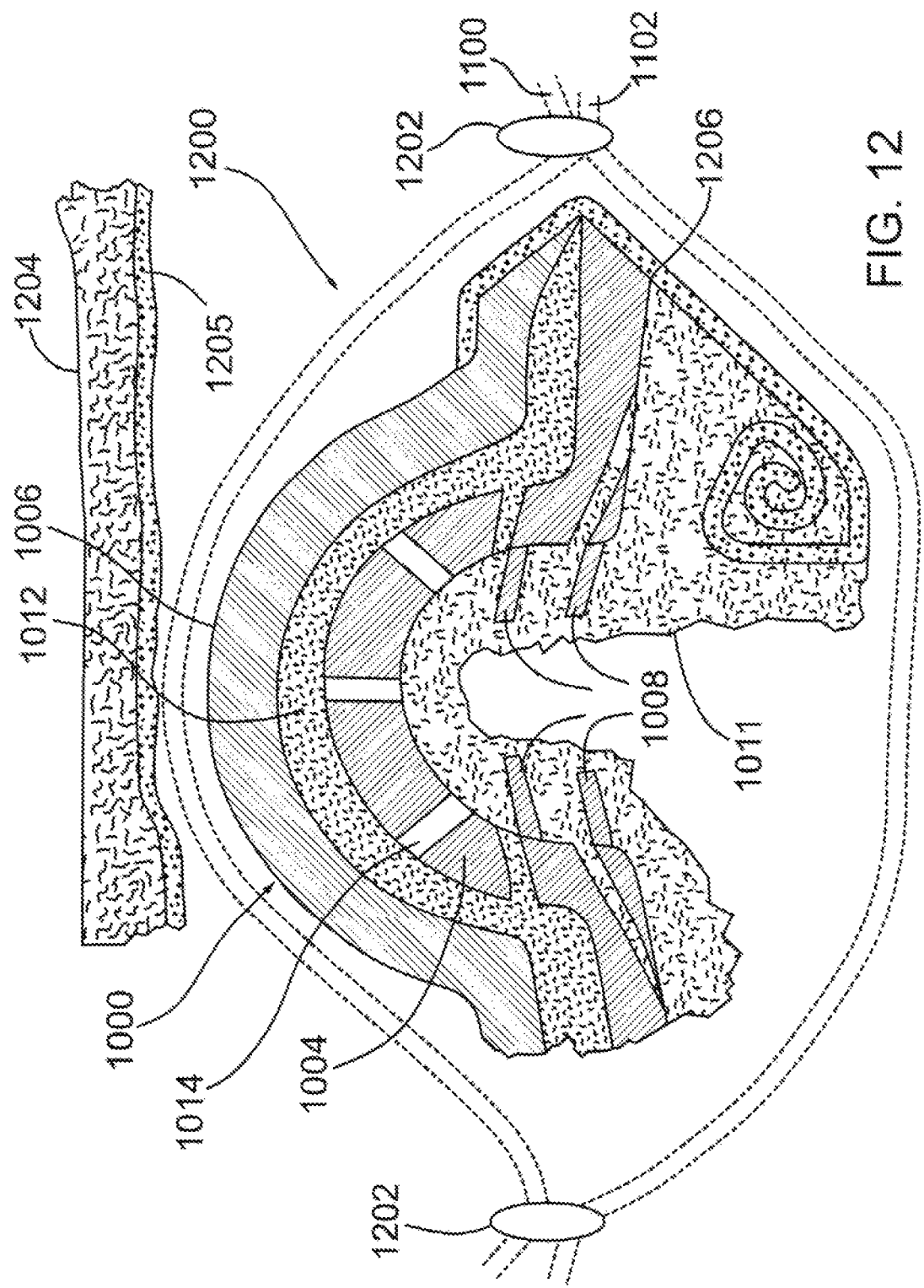
FIG. 12 is an example embodiment of a sheathed multi-layered dressing integrating the protrusion of FIG. 10.

FIG. 12 is an example embodiment of a sheathed multi-layered dressing integrating the protrusion 1000 of FIG. 10. In this example, the sheath 1200 can be, for example, a tubinette or tubular gauze, stretchy in nature, such that the dressing is suitable for ulcer compression therapy. Different sections of protrusions within the sheath 1200 can be separated using stitches 1202 to form separate compartments. Only one protrusion 1000 is shown in this example as stitched within its own section of tubinette or tubular gauze, but additional protrusions can be stitched within proximate sections of the tubinette or tubular gauze as well to construct the full dressing. Compression of the sheath 1200 is achieved using a compressive layer 1204, for example a Coban™ compression layer. An optional second compressive layer 1205 can also be used for compression therapy. The compressive layers 1204, 1205 can be made of breathable material, for example, some types of elastics or cotton, and can be adhered together using adhesives, welding, sewing, thermoforming, or a combination of these or other techniques.

The absorptive layer 1011, first outer layer 1004, spaced rings 1008, absorptive layer 1012, second outer layer 1006, and holes 1014 can all function in a manner similar to that as described in FIGS. 10 and 11. However, the perimeter of the dressing differs from that as described in FIG. 11. Instead of the adhesive layer 1102 described in FIG. 11, an extended spiral edge layer 1206 adheres the first outer layer 1004 and second outer layer 1006. The absorptive layer 1011 extends along the entire length of the spiral edge layer 1206, increasing the amount of exudate that can be collected at the edges of the sheathed dressing. Once the exudate becomes trapped within the spiral edge layer 1206, it is no longer able to return to the area of the wound as it would need to counteract gravitational forces to do so. The spiral edge layer 1206 also becomes heavier than the protrusion 1000 portion of the sheathed multi-layered dressings once it absorbs exudate. Further, the absorptive layer 1011 can be made of cotton mixed with a powdered superabsorbent polymer (SAP) which assists in keeping the exudate or liquid away from the wound and avoids significant lateral wicking. The absorptive layer 1011 can also be made of foam woven or non-woven with hypoallergenic substrates.

Figure 13B:
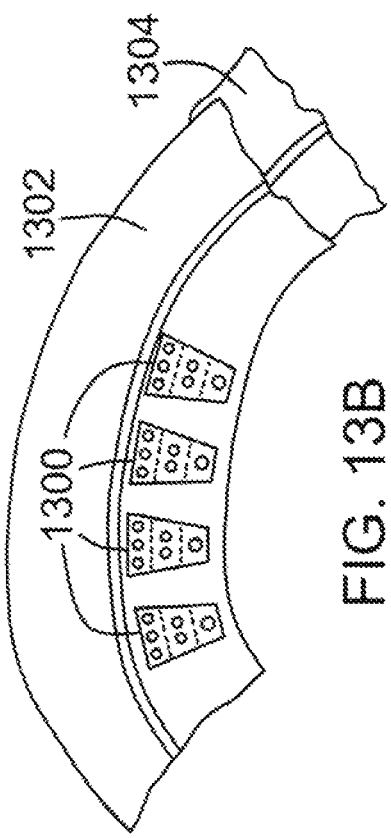
FIGS. 13A and 13B show an example embodiment of a wrap-style dressing integrating segments of protrusions similar to the protrusions of FIGS. 5, 6, and 10.
Figure 13A:
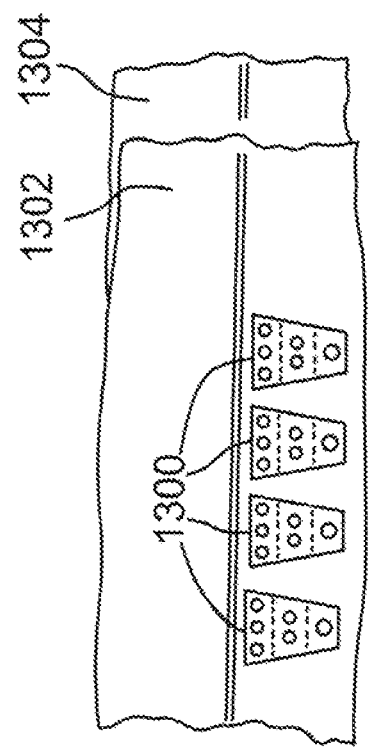

FIGS. 13A and 13B show an example embodiment of a wrap-style dressing integrating segments 1300 of protrusions similar to the protrusions of FIGS. 5, 6, and 10. In this example, multiple segments 1300 of protrusions can be spread along a first surface 1302 of a wrap-style dressing, for example, along a stretchy gauze material suitable for wrapping, for example, body parts such as arms, legs, wrists, or ankles. The segments 1300 of protrusions in this example are installed only along half of the width of the first surface 1302 because wrap-style dressings are configured such that effective compression is achieved when approximately half of the width of the dressing is overlapped with each rotation around a body part. The second surface 1304 of the wrap-style dressing can be an alternative material, for example, a breathable cotton, to ensure proper evaporation.

FIG. 13A shows the wrap-style dressing in a straight configuration, before application to a patient. FIG. 13B shows the flexibility of the wrap-style dressing, curved in a manner that could be experienced when a medical provider begins to apply the wrap-style dressing to a patient. The spacing between the segments 1300 of protrusions should be such that proper absorption of liquids or exudate and sufficient compression are possible given the type of wound being treated while at the same time allowing the flexibility needed for the wrap-style dressing to be applied to various shapes of body parts.

Figure 14A:
FIGS. 14A-F show a sequence representing the application of a wrap-style dressing, a layer of which includes segments of protrusions similar to the protrusions of FIGS. 5, 6, and 10 to a limb.
Figure 14B:
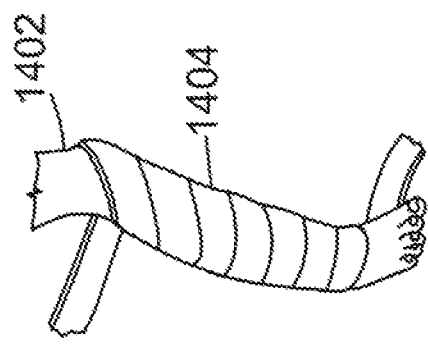
Figure 14C:
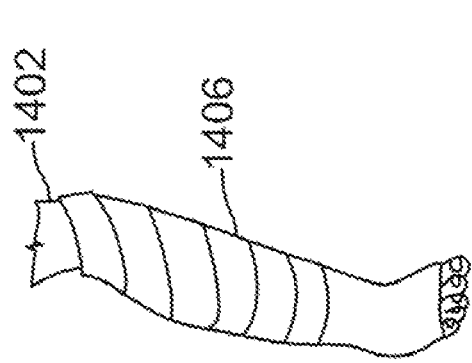
Figure 14D:
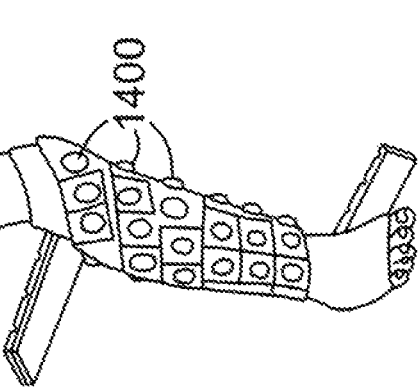
Figure 14E:
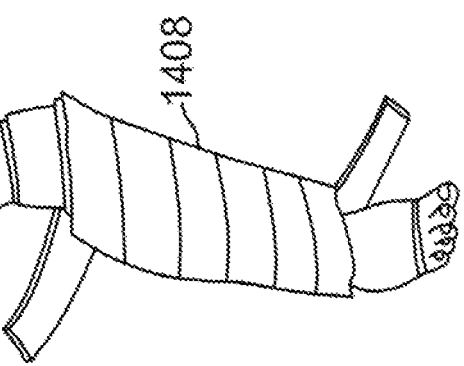
Figure 14F:
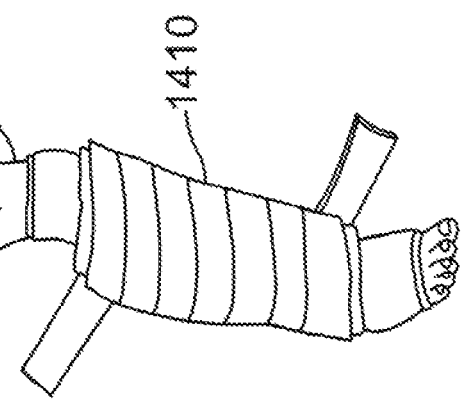

FIGS. 14A-F show a sequence representing the application of a wrap-style dressing, a layer of which includes segments of protrusions 1400 similar to the protrusions of FIGS. 5, 6, and 10 to a limb 1402. FIG. 14A shows a naked limb, in this example, a leg and foot of a patient. No wounds are shown, but it can be understood that the wound can be present. FIG. 14B shows an under-wrap 1404, for example, of cotton. FIG. 14C shows a tubular wrap 1406, for example, a stoikinette applied over the under-wrap 1404. FIG. 14D shows the application of the wrap-style dressing including protrusions 1400 as described at length in previous embodiments of the disclosure. The wrap-style dressing is applied to the leg, but not the foot, as the compression caused by a patient walking on the protrusions 1400 without additional support could cause the protrusions 1400 to collapse. FIG. 14E shows the addition of a compression band 1408 above the wrap-style dressing of protrusions 1400. FIG. 14F shows the addition of a secondary compression band 1410, for example, a COBAN™ layer. The proper application of the complete wrap-style dressing allows for successful compression therapy of a wound, for example, an ulcer.

FIGS. 15A-E show a sequence representing the construction of a multi-layered dressing such as the multi-layered dressing shown in FIG. 12. FIG. 15A shows a tubular tubinette 1500, for example, of cotton, the serves as the outer sheath of the multi-layered dressing. The tubinette 1500 is expandable. FIG. 15B shows a perforated layer of hypoallergenic material 1502. FIG. 15C shows a sectioned, or quilted, multi-layered wound dressing 1504 formed of multiple protrusions 1506 in the style of the protrusions shown in FIG. 12. FIG. 15D shows how the three components from FIGS. 15A-15C are constructed, in the style of a pocket sandwich, for example. The hypoallergenic material 1502 is disposed on top of the multi-layered wound dressing 1504 and the combination of these components can be inserted into the tubinette 1500. FIG. 15E shows the combined construction of multiple tubinettes 1500, each containing a certain length and width of hypoallergenic material 1502 and multi-layered wound dressing 1504. Each separate assembly can be combined, for example, using lines of stitches 1508. The multi-layered dressing shown in FIG. 15E can be used to cover the foot of a limb, for example, the limb shown in FIGS. 14A-F based on its increased flexibility.

Figures 16A, 16B:
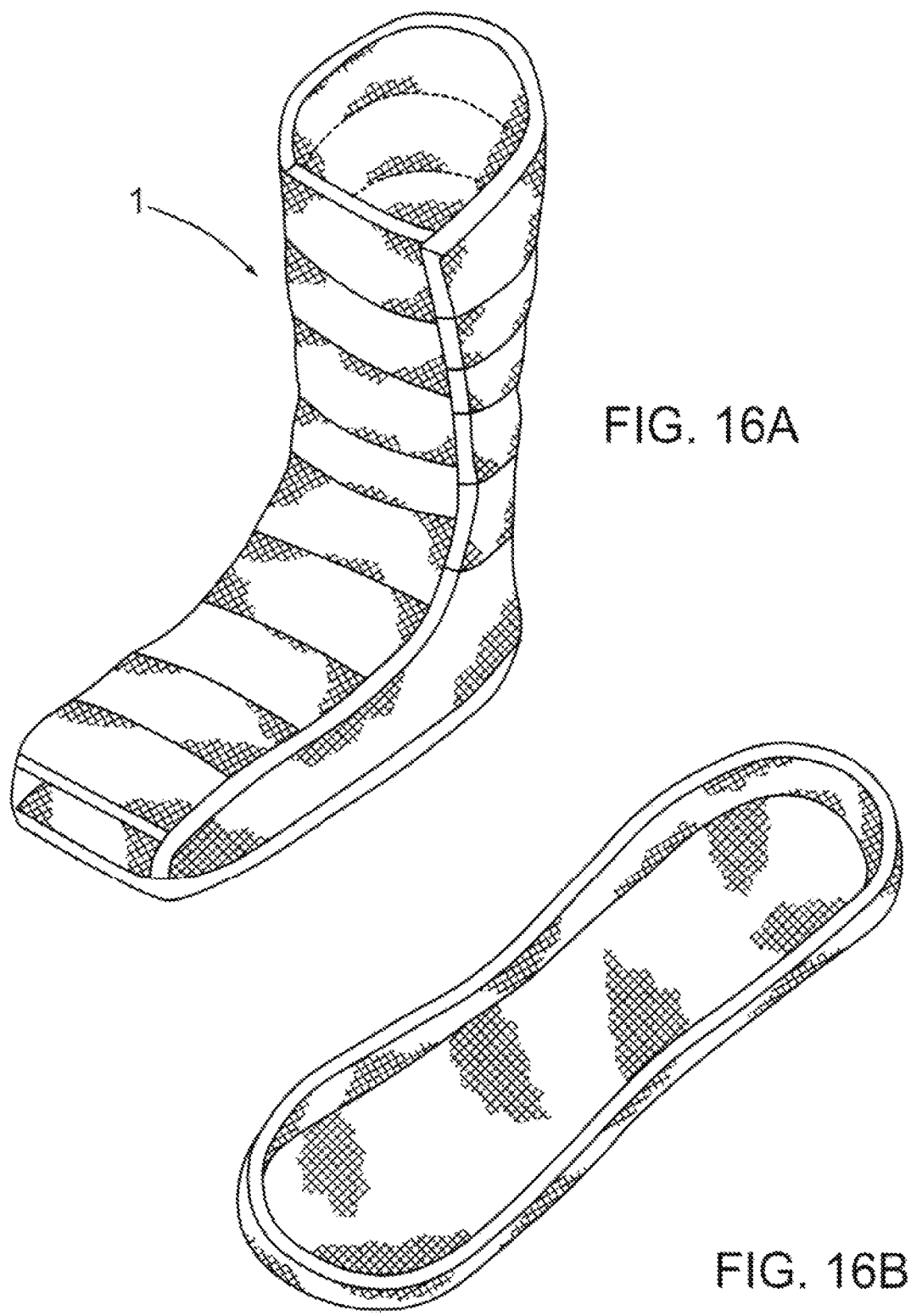
FIGS. 16A-D show multi-layered dressings similar to those described in FIGS. 12 and 15A-E configured for use in a walking boot or brace.
Figure 16C:
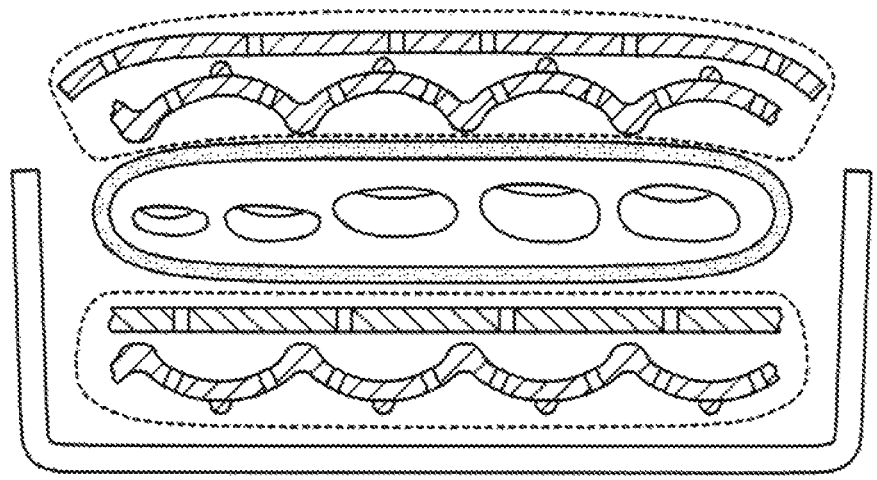
Figure 16D:
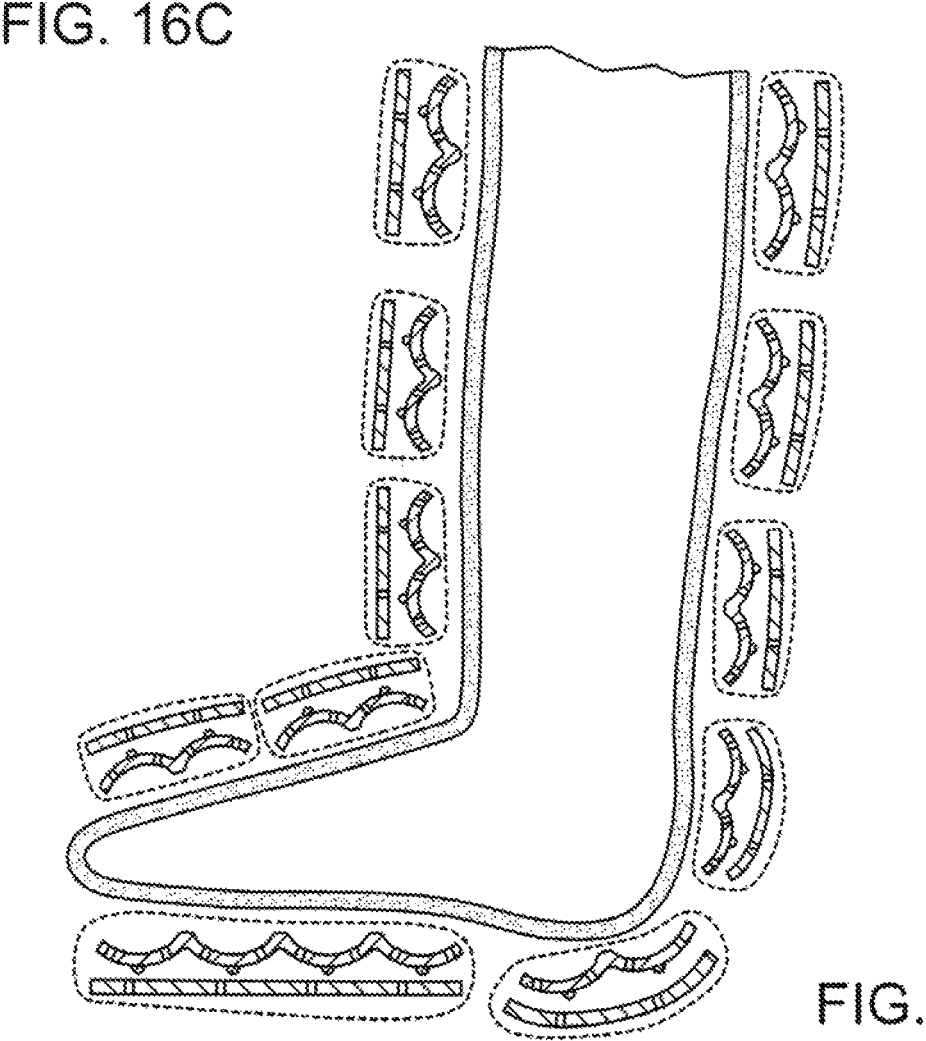

FIGS. 16A-D show multi-layered dressings similar to those described in FIGS. 12 and 15A-E configured for use in a walking boot or brace. FIG. 16A shows a compound boot-shape dressing configured in two parts, one part for situation below the leg and foot and the other part for situation above the leg and foot of a patient. The boot-shape can be formed of connected sections of tubular, enclosed multi-layered dressings, the connections established by stitching, welding, adhesive, or any other method. FIG. 16B shows a top view of an internal base for the boot-shaped dressing, formed of connected tubinettes including separated sections of protrusions. FIG. 16C shows a front cross-section of the boot-shape dressing as applied to a patient's foot. The internal base of FIG. 16B is disposed below the foot and a compression-style dressing is disposed above the foot, both dressings including protrusions as described in previous embodiments. FIG. 16D shows a side cross-section of the boot-shape dressing as applied to the entire lower limb of a patient, the various layers wrapped on the lower limb in a manner consistent with providing compression therapy, for example, to an ulcerous wound.

Figure 17:
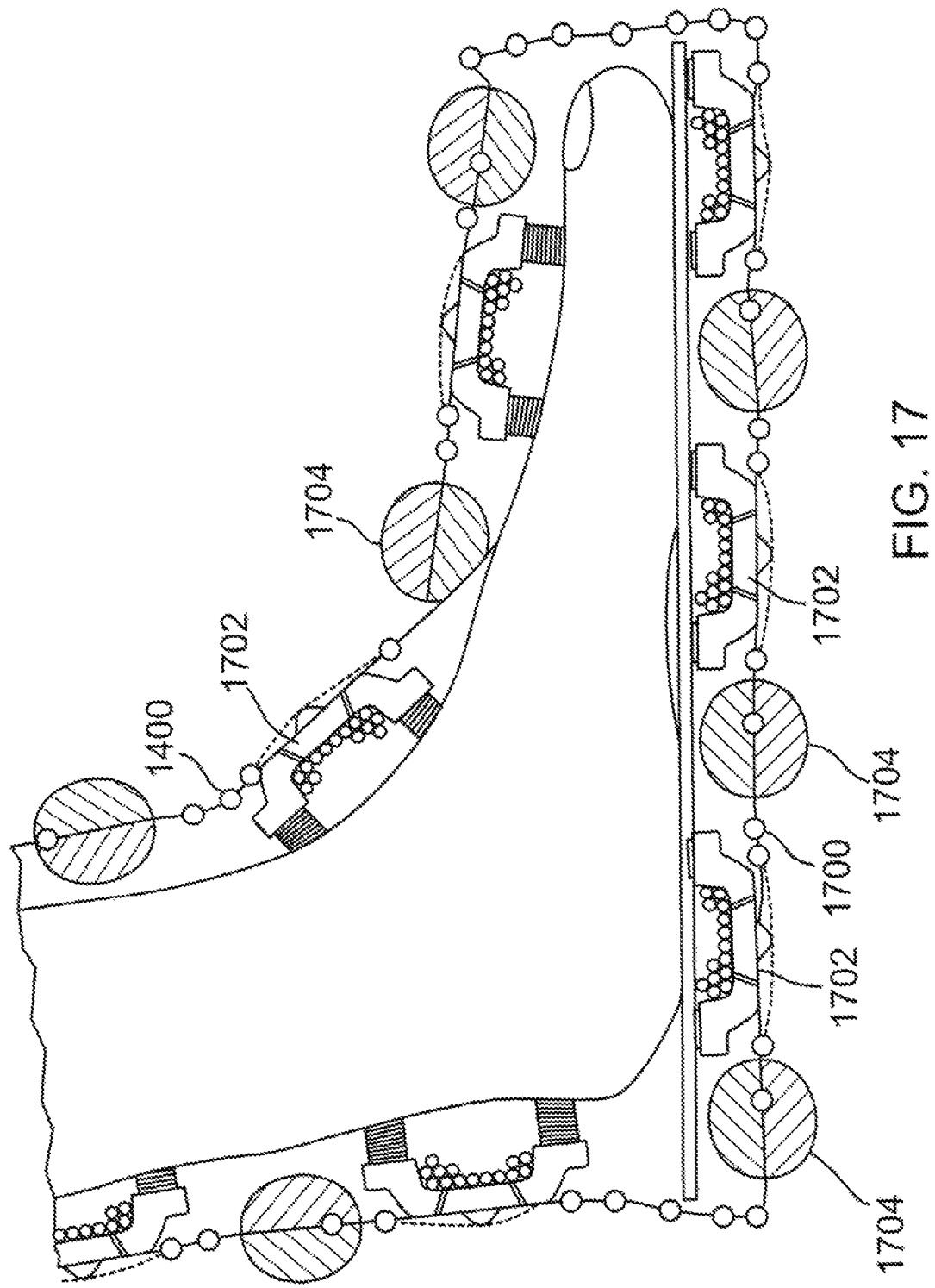
FIG. 17 shows a sock-style dressing configured for use with the wrap-style dressings of FIGS. 13A-B and 14A-F.

FIG. 17 shows a sock-style dressing configured for use with the wrap-style dressings of FIGS. 13A-B and 14A-F. Once the wrap-style dressing is partially applied, the sock-style dressing can be pulled onto a patient's foot, for example, in the same manner as putting on a sock. The wrap-style and sock-style dressings can thus be used in combination to provide compression therapy to a patient's lower limb while at the same time allowing the patient to apply pressure to the foot, for example, using a walking cast.

The sock-style dressing can include a stretchy layer 1700, for example, of Surgilast™ material. The flexibility of the stretchy layer 1700 allows the dressing to be applied to an area of the body that can experience constant motion, such as the foot. Spaced protrusions 1702, for example, similar in style to protrusions described in previous embodiments, can be disposed below the stretchy layer 1700, proximate to the patient's foot for use in wound treatment and compression therapy. In addition, supportive spacers 1704 can be coupled to the stretchy layer 1700 between the spaced protrusions 1702. The spacers 1704 can be spherical in shape, with one half of each spacer connected to the other half through the stretchy layer 1700. The spacers 1704 can be formed of durable materials, such as metal alloy or cork, of sufficient strength to support the patient walking on the sock-style dressing while additionally keeping the protrusions 1702 from being crushed by the force of the patient's gait.

The sock-style dressing can be used in combination with a wrap-style dressing on a patient's leg as described above, used underneath a walking cast when the patient has a wound on the foot, used with a prosthetic device to treat a wound experiencing force when in use with the prosthetic, or used under an elastic-wrap, for example, Coban™ for compressive therapy. As with previous embodiments, a layer of cotton or stokinette can be applied to the wound before pulling on the stock-style dressing.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed is:

1. A perforated wound dressing, comprising:
 a first layer including a first set of spaced protrusions, each protrusion comprising an underside configured to face a wound and shaped to receive medication for treating the wound;

a second layer overlying and directly adjacent to the first layer, including a second set of spaced protrusions, the second set of spaced protrusions being of similar shape to and aligned with the first set of spaced protrusions and wherein the second layer is harder than the first layer such that the second set of spaced protrusions better withstand compression; and a plurality of cylindrical holes defined through the first layer and the second layer, the holes configured to allow evaporation of exudate from the wound to pass through the perforated wound dressing in a direction substantially perpendicular to the wound's surface.

2. The perforated wound dressing of claim 1, wherein the plurality of holes are located between the spaced protrusions.

3. The perforated wound dressing of claim 1, wherein the first layer comprises medical silicone.

\* \* \* \* \*